United States Patent
Cecchi

(10) Patent No.: US 6,867,220 B2
(45) Date of Patent: *Mar. 15, 2005

(54) PHENOXYPROPANOLAMINES, METHOD FOR PRODUCING THEM AND PHARMACEUTICAL COMPOSITIONS CONTAINING THEM

(75) Inventor: Roberto Cecchi, Lodi (IT)

(73) Assignee: Sanofi-Synthelabo, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 10/149,497

(22) PCT Filed: Dec. 14, 2000

(86) PCT No.: PCT/FR00/03535

§ 371 (c)(1),
(2), (4) Date: Jun. 12, 2002

(87) PCT Pub. No.: WO01/43744

PCT Pub. Date: Jun. 21, 2001

(65) Prior Publication Data

US 2003/0040530 A1 Feb. 27, 2003

(30) Foreign Application Priority Data

Dec. 17, 1999 (FR) .............................. 99 15932
Dec. 17, 1999 (FR) .............................. 99 15931

(51) Int. Cl.⁷ ..................... A61K 31/445; C07D 401/12
(52) U.S. Cl. .................... 514/318; 514/329; 514/331; 546/193; 546/223; 546/232
(58) Field of Search .............................. 514/318, 329, 514/331; 546/193, 223, 232

(56) References Cited

U.S. PATENT DOCUMENTS

| | | | |
|---|---|---|---|
| 5,627,196 A | | 5/1997 | Audia et al. ................. 514/323 |
| 5,948,792 A | * | 9/1999 | Tsuchiya ..................... 514/317 |
| 6,444,685 B1 | * | 9/2002 | Sun et al. .................... 514/317 |
| 6,525,202 B2 | * | 2/2003 | Hu et al. ..................... 546/223 |
| 2003/0144326 A1 | * | 7/2003 | Hu et al. ..................... 514/326 |

FOREIGN PATENT DOCUMENTS

| | | |
|---|---|---|
| DE | 35 24 955 A | 1/1986 |
| EP | 095 454 A | 11/1983 |
| WO | WO 99 52872 A | 10/1999 |
| WO | WO 99 65895 A | 12/1999 |

OTHER PUBLICATIONS

Greene "Protective groups in organic synthesis" Wiley & Sons, p. 218–19, 232, 236 (1982).*
Spatola et al. "Amide bond surrogates . . . " Tetrahedron v.44 p. 821–826(1988).*
Fisher et al. "Substituted sulfonamides . . . " CA 125:221588 (1996).*
Brazzell et al. "Treatment of glaucoma . . . " CA 126:1213 (1996).*
Wermuth C. G. "The practice of medicinal chemistry" Acad. pres. p. 207–217 (1996).*
Hu et al. "Preparation of cyclic amine . . . " CA 136:134676 (2002).*
Shey et al. "Liquid phase combinatoryal . . . " CA 130:296679 (1999).*
Mitsuya et al. "A potent long acting . . . " CA 134:147471 (2000).*

(List continued on next page.)

Primary Examiner—Celia Chang
(74) Attorney, Agent, or Firm—Michael D. Alexander

(57) ABSTRACT

The invention relates to compounds of formula (I)

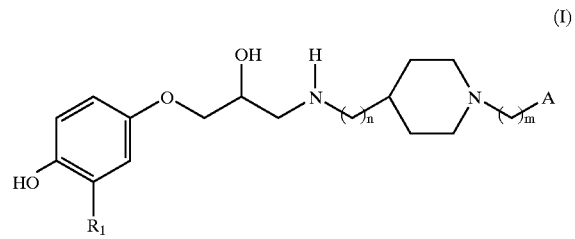

(I)

where
$R_1$ represents a hydrogen or halogen atom or an $-S(O)_z-(C_1-C_4)$alkyl, $-S(O)_z-(C_1-C_4)R_3$, $-SO_2-NH-(C_1-C_4)$alkyl, $-NHCO(C_1-C_4)$ alkyl, $-CO(C_1-C_4)$ alkyl or $-NHSO_2-(C_1-C_4)$alkyl group;
m and n independently represent 0, 1 or 2;
A represents a group of formula (a) or (b):

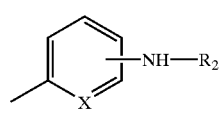

(a)

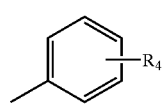

(b)

where
X is N or CH;
$R_2$ represents an $-SO_2-R_3$, $-CO-R_3$ or $-CO-(C_1-C_4)-$alkyl group;
$R_3$ represents a phenyl group, optionally substituted by a $(C_1-C_4)$alkyl or $(C_1-C_4)$alkoxy group, one or two halogen atoms or a heterocycle;
$R_4$ represents a hydrogen or halogen atom or a $(C_1-C_6)$alkyl, $(C_1-C_4)$alkoxy, $-COOH$, $-COO(C_1-C_4)$alkyl, $-CN$, $-CONR_5R_6$, $-NO_2$, $-NHSO_2(C_1-C_4)$alkyl or $-SO_2NR_5R_6$ group;
z is 1 or 2;
$R_5$ and $R_6$ independently represent a hydrogen atom or a $(C_1-C_4)$alkyl, phenyl or phenyl $(C_1-C_4)$alkyl group;
and their salts or solvates, to a process for their preparation, to synthetic intermediates and to the pharmaceutical compositions comprising them.

25 Claims, No Drawings

OTHER PUBLICATIONS

Sum et al. "prepartion of (2–hydroethylamino)cyclic-amino . . . " CA 136:134678 (2002).*

M. Hori et al.; Journal of Organic Chemistry, vol. 63, no. 3; pp 889–894 (1998).

Chemical Abstract No. 131:299455 (1999).
Derwent Patent Abstract No. 198605 (2002).
Derwent Patent Abstract No. 198349 (2002).
Derwent Patent Abstract No. 200011 (2002).

* cited by examiner

PHENOXYPROPANOLAMINES, METHOD FOR PRODUCING THEM AND PHARMACEUTICAL COMPOSITIONS CONTAINING THEM

The present invention relates to novel phenoxypropanolamines, to the pharmaceutical compositions comprising them, to a process for their preparation and to intermediates in this process.

BE 902897 discloses aryloxypropanolamines carrying a (4-piperidinin-1-yl)-substituted group on the amine, these compounds having a beta-1-blocking and alpha-blocking activity.

J. Org. Chem., 1988, 63, 889–894, describes other aryloxypropanolamines carrying a (4-piperidin-1-yl)-substituted group on the amine.

It has now been found that novel phenoxypropanolamines carrying a (4-piperidin-1-yl)-substituted group on the amine have an agonist activity with respect to beta-3-adrenergic receptors.

The beta-3-adrenergic receptor has formed the subject of numerous studies targeted at synthesizing compounds which are agonists with respect to this receptor, these compounds exerting a significant antiobesity and antidiabetic effect in man, as described, for example, by Weyer, C et al., Diabetes Metab., 1999, 25(1), 11–21.

Thus, the present invention relates, according to one of its aspects, to phenoxy-propanolamines of formula (I)

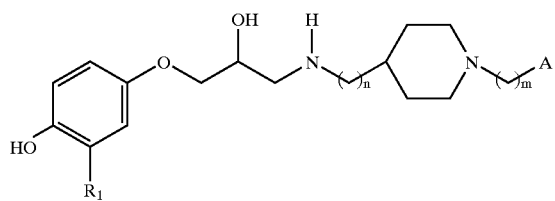

(I)

where
$R_1$ represents a hydrogen or halogen atom or an $-S(O)_z-(C_1-C_4)$alkyl, $-S(O)_z-(C_1-C_4)R_3$, $-SO_2-NH-(C_1-C_4)$alkyl, $-NHCO(C_1-C_4)$alkyl, $-CO(C_1-C_4)$alkyl or $-NHSO_2-(C_1-C_4)$alkyl group;
m and n independently represent 0, 1 or 2;
A represents a group of formula (a) or (b):

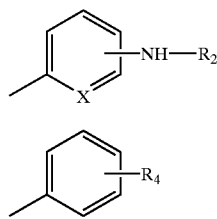

where
x is N or CH;
$R_2$ represents an $-SO_2-R_3$, $-CO-R_3$ or $-CO-(C_1-C_4)$-alkyl group;
$R_3$ represents a phenyl group, optionally substituted by a $(C_1-C_4)$alkyl or $(C_1-C_4)$alkoxy group, one or two halogen atoms or a heterocycle;
$R_4$ represents a hydrogen or halogen atom or a $(C_1-C_6)$alkyl, $(C_1-C_4)$alkoxy, $-COOH$, $-COO(C_1-C_4)$alkyl, $-CN$, $-CONR_5R_6$, $-NO_2$, $-NHSO_2(C_1-C_4)$alkyl or $-SO_2NR_5R_6$ group;

z is 1 or 2;
$R_5$ and $R_6$ independently represent a hydrogen atom or a $(C_1-C_4)$alkyl, phenyl or phenyl$(C_1-C_4)$alkyl group;
and their salts or solvates.

In the present description, the terms "$(C_1-C_4)$alkyl" and "$(C_1-C_6)$alkyl" denote monovalent radicals of a respectively $C_1-C_4$ and $C_1-C_6$ hydrocarbon comprising a straight or branched saturated chain.

In the present description, the term "halogen" denotes an atom chosen from chlorine, bromine, iodine and fluorine.

The salts of the compounds of formula (I) according to the present invention comprise both addition salts with pharmaceutically acceptable inorganic or organic acids, such as the hydrochloride, hydrobromide, sulfate, hydrogensulfate, dihydrogenphosphate, citrate, maleate, tartrate, fumarate, gluconate, methanesulfonate, 2-naphthalenesulfonate, and the like, and addition salts which make possible suitable separation or crystallization of the compounds of formula (I), such as the picrate, the oxalate or the addition salts with optically active acids, for example camphorsulfonic acids and mandelic or substituted mandelic acids.

When the compounds of formula (I) possess a free carboxyl group, the salts also comprise the salts with inorganic bases, preferably those with alkali metals, such as sodium or potassium, or with organic bases.

The optically pure stereoisomers and the mixtures of isomers of the compounds of formula (I), due to the asymmetric carbons or to the sulfinyl group, when z is 1 in the meaning of $R_1$, in any proportion, form part of the present invention.

Preferred compounds are those where the $(C_1-C_4)$alkyl group is a methyl or ethyl group.

Other further preferred compounds are those where n and m are zero.

Preferred compounds of the present invention comprise the compounds of formula (I) where A is a group (a), X is N and the $NHR_2$ group is in the 5 position of the pyridine.

Other preferred compounds of the present invention comprise the compounds of formula (I) where A is a group (b) and the $R_4$ group is in the 4 position of the benzene.

Other preferred compounds are those where A is a group (b) and $R_4$ is chosen from $-COOH$, $-COO(C_1-C_4)$-alkyl, $-CN$, $-NO_2$, $-CONR_2R_3$, $-NHSO_2-(C_1-C_4)$alkyl or $-SO_2NR_5R_6$.

The compounds of formula (I) can be prepared by treating a compound of formula (II)

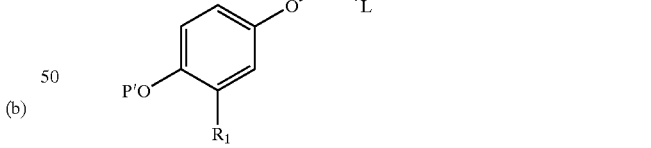

(II)

in which $R_1$ is as indicated above, P' is a protective group and L is a group of formula (c) or (d)

(c)

(d)

where Gp is a leaving group, such as tosylate, mesylate or a halogen atom, with an amine of formula (III)

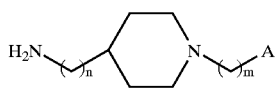
(III)

in which n and m are as defined above, the group P' being cleaved according to conventional methods and the compound of formula (I) thus obtained optionally being converted into one of its salts.

More particularly, the reaction between the compounds of formula (II) and (III) is carried out in an organic solvent, such as a lower alcohol, for example methanol, ethanol and isopropanol; dimethyl sulfoxide; a linear or cyclic ether; or an amide, such as dimethylformamide or dimethylacetamide; using at least equimolecular amounts of the reactants, optionally in a slight excess of amine.

The temperature of the reaction is between ambient temperature and the reflux temperature of the solvent chosen.

Use may be made, as protective groups P', of the conventional protective groups for hydroxyl groups, such as, for example, methoxyethoxymethyl (MEM), benzyl, benzoyl or silyl ethers, such as, for example, the tert-butyldimethylsilyl ether (TBDMS).

The cleaving of these protective groups is carried out according to the standard methods according to the protective group chosen and according to the reactivity of the other groups present, in the case of the benzyl group, for example, by hydrogenation in the presence of a catalyst, such as Pd/C, in a suitable solvent; in the case of MEM or of TBDMS, it is also possible to use an acid, such as trifluoroacetic acid; in the case of benzoyl, a transesterification reaction with an alkanol in a basic medium can be carried out.

The epoxides of formula (II) are compounds which are known in the literature or alternatively they can be prepared by processes analogous to those described in the literature. Some epoxides of formula (II) are, for example, disclosed in WO 96/04233 and in U.S. Pat. No. 4,396,629.

Some of the amines of formula (III) are novel compounds and constitute another aspect of the present invention.

Thus, according to another of its aspects, the present invention relates to amines of formula (III')

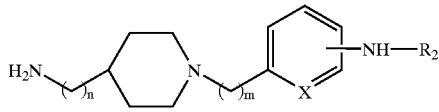
(III')

where n, m, X and $R_2$ are as defined above, and their salts or solvates.

These amines can be prepared by reaction of the compounds of formula (IV)

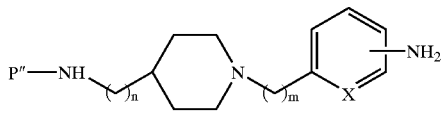
(IV)

in which P" is a protective group, such as tert-butoxycarbonyl or benzyloxycarbonyl, with a radical Cl—$R_2$, where $R_2$ is as described above and Hal is a halogen atom, in a suitable solvent, such as, for example, pyridine, dimethylformamide or dimethyl sulfoxide, and by removal of the group P" by hydrogenation or by treatment in an acidic medium, such as hydrochloric acid in ethyl acetate or in ethanol.

The starting amines of formula (IV) can be prepared by reaction of suitable pyridines of formula (V)

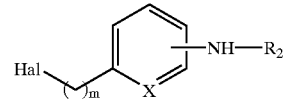
(V)

where Hal represents a halogen atom and $R_2$ and m are as defined above, with a piperidine of formula (VI) below

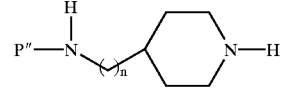
(VI)

where n is as defined above and P" represents a protective group, in an organic solvent in the presence of a base.

Use may indeed be made, as reaction solvent, of, for example, dimethylformamide, pyridine, dimethyl sulfoxide, a linear or cyclic ether, or a chloridated solvent, such as dichloromethane.

Use may be made, as base, of, for example, an alkaline hydroxide, an alkaline carbonate, such as potassium carbonate, or a tertiary amine, such as triethylamine.

The above condensation reaction is completed in a few hours, normally in 2–12 hours.

The reaction temperature is between ambient temperature and the reflux temperature of the solvent chosen.

Use may be made, as protective groups P", of, for example, the protective groups indicated for the products of formula (IV).

The cleaving of these protective groups is carried out according to the standard methods described for the protective group chosen; in the case of tert-butoxycarbonyl, for example, the cleaving is normally carried out by acid hydrolysis.

Other novel intermediates which form part of the present invention are the amines of formula (III")

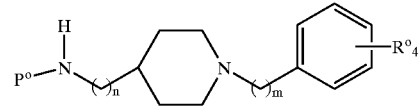
(III")

where
P° is a tert-butoxycarbonyl group;
n and m are 0, 1 or 2;
$R°_4$ is a group chosen from —COOH, —COO($C_1$–$C_4$)-alkyl, —CONR°$_5$R°$_6$ and —NHSO$_2$($C_1$–$C_4$)alkyl;
R°$_5$ and R°$_6$ independently represent a hydrogen atom or a ($C_1$–$C_4$)alkyl group;
and their salts or solvates.

Compounds of formula (III") which are particularly preferred are those where n is 0, m is 0 or 1 and $R°_4$ is —COO($C_1$–$C_4$)alkyl.

The compounds of formula (III") can be prepared analogously to the above compounds (IV).

The compounds of formula (I) have shown a very powerful affinity with respect to beta-3 receptors.

The activity of the compounds of the present invention with respect to beta-3 agonist activity was demonstrated using in vitro tests on the human colon according to the method disclosed in EP-B-436 435 and in T. Croci et al., Br. J. Pharmacol., 1997, 122, 139P.

More particularly, it has been found that the compounds of formula (I) are much more active on the isolated colon than on the atrium and on the trachea.

These surprising properties of the compounds of formula (I) make it possible to envisage their use as medicaments with a beta-3 action.

Furthermore, the compounds of formula (I) are not very toxic; in particular, their acute toxicity is compatible with their use as medicaments for the treatment of diseases in which compounds having an affinity for the beta-3 receptor find application. The compounds of formula (I) and their pharmaceutically acceptable salts can therefore be indicated, for example, in the treatment of gastrointestinal diseases, such as irritable bowel syndrome (IBD), as modulators of intestinal motricity, or as lipolytics, antiobesity agents, antidiabetics, psychotropics, antiglaucoma agents, cicatrizants, antidepressants or tocolytics.

The use of the compounds of formula (I) above, and that of their pharmaceutically acceptable salts and solvates, for the preparation of above medicaments constitutes a subsequent aspect of the present invention.

For such a use, an effective amount of a compound of formula (I) or of one of its pharmaceutically acceptable salts and solvates is administered to the mammals who require such a treatment.

The compounds of formula (I) above and their pharmaceutically acceptable salts and solvates can be used at daily doses of 0.01 to 20 mg per kilo of body weight of the mammal to be treated, preferably at daily doses of 0.1 to 10 mg/kg. In man, the dose can preferably vary from 0.5 mg to 1 500 mg per day, in particular from 2.5 to 500 mg, according to the age of the subject to be treated, the type of treatment, prophylactic or curative, and the seriousness of the condition. The compounds of formula (I) are generally administered as a dosage unit of 0.1 to 500 mg, preferably of 0.5 to 100 mg, of active principle, one to five times daily.

Said dosage units are preferably formulated in pharmaceutical compositions in which the active principle is mixed with a pharmaceutical excipient.

Thus, according to another of its aspects, the present invention relates to pharmaceutical compositions including, as active principle, a compound of formula (I) above or one of its pharmaceutically acceptable salts and solvates.

In the pharmaceutical compositions of the present invention for oral, sublingual, subcutaneous, intramuscular, intravenous, topical, transdermal or rectal administration, the active ingredients of formula (I) above and their pharmaceutically acceptable salts and solvates can be administered in unit administration forms, as a mixture with conventional pharmaceutical vehicles, to animals and human beings for the treatment of the above said conditions. The appropriate unit administration forms comprise oral forms, such as tablets, gelatin capsules, powders, granules and solutions or suspensions to be taken orally, sublingual and buccal administration forms, subcutaneous, intramuscular or intravenous administration forms, local administration forms and rectal administration forms.

When a solid composition is prepared in the form of tablets, the main active ingredient is mixed with a pharmaceutical vehicle, such as gelatin, starch, lactose, magnesium stearate, talc, gum arabic or the like. The tablets can be coated with sucrose or other appropriate materials or can be treated so that they have a prolonged or delayed activity and so that they continuously release a predetermined amount of active principle.

A preparation in the form of gelatin capsules is obtained by mixing the active ingredient with a diluent and by pouring the mixture obtained into soft or hard gelatin capsules.

A preparation in the syrup or elixir form can comprise the active ingredient in conjunction with a sweetener, preferably a calorie-free sweetener, methylparaben and propylparaben as antiseptics, and an appropriate colorant and flavoring.

The water-dispersible powders or granules can comprise the active ingredient as a mixture with dispersing agents, wetting agents or suspending agents, such as polyvinylpyrrolidone, and with sweeteners or flavor enhancers.

For local administration, the active principle is mixed in an excipient for the preparation of creams or ointments or is dissolved in a vehicle for intraocular administration, for example in the form of an eyewash.

For rectal administration, recourse is had to suppositories which are prepared with binders which melt at the rectal temperature, for example cocoa butter or polyethylene glycols.

For parenteral administration, use is made of aqueous suspensions, saline solutions or sterile injectable solutions which comprise pharmacologically compatible dispersing and/or wetting agents, for example propylene glycol or butylene glycol.

The active principle can also be formulated in the form of microcapsules, optionally with one or more vehicles or additives.

According to another of its aspects, the present invention relates to a method for the treatment of the pathologies which are improved by a beta-3-agonist action which comprises administering a compound of formula (I) or one of its pharmaceutically acceptable salts or solvates.

The compounds of formula (I), in particular the compounds (I) labeled with an isotope, can also be used as laboratory tools in biochemical assays.

The compounds of formula (I) bind to the beta-3-adrenergic receptor. These compounds can therefore be used in a standard binding assay, in which use is made of an organic tissue in which this receptor is particularly abundant, and the amount of compound (I) displaced by a test compound is measured, in order to evaluate the affinity of said compound with respect to binding sites of this specific receptor.

Another specific subject matter of the present invention is thus a reagent which can be used in biochemical assays, which comprises at least one suitably labeled compound of formula (I).

The examples which follow give a better illustration of the invention.

Preparation 1

4-(tert-Butoxycarbonylamino)piperidine.

25 g (0.13 mol) of 4-amino-1-benzylpiperidine, 36.2 ml (0.26 mol) of triethylamine and 31.2 g (0.143 mol) of di-tert-butyl dicarbonate are mixed in 200 ml of dimethylformamide at ambient temperature for 2 hours. The mixture is poured into water, extraction is carried out with ethyl acetate and washing is carried out with water, and the product thus obtained is crystallized from 200 ml of isopropyl ether. 33 g of 1-benzyl-4-(tert-butoxycarbonylamino) piperidine are obtained and are hydrogenated in a mixture of 200 ml of ethanol and 100 ml of tetrahydrofuran in the presence of 3 g of 10% Pd/C. After filtering off the catalyst, the title compound is isolated.

M.p. 157–160° C.

Preparation 2

4-tert-Butoxycarbonylamino-1-(4-ethoxycarbonylphenyl-methyl)piperidine

A mixture of 2.01 g (0.010 mol) of the product obtained in preparation 1 and 2 g (0.010 mol) of 4-chloromethyl-ethoxycarbonylbenzene in 40 ml of dimethylformamide is heated with stirring for 6 hours at 50° C. The mixture is poured into water, extraction is carried out with ethyl acetate and washing is carried out with water. The product is filtered off and dried. The crude product thus obtained is purified by flash chromatography, elution being carried out with a cyclohexane/ethyl acetate=1:1 mixture. The title compound is obtained.

M.p. 74–76° C.

Preparation 3

4-Amino-1-(4-ethoxycarbonylphenylmethyl)piperidine

The product obtained by preparation 2 is heated at reflux for 5 hours in a solution comprising 15 ml of ethyl acetate and 15 ml of hydrochloric acid in ethyl acetate (about 3N). After cooling, filtration is carried out, washing with acetone is carried out and the product is dried under reduced pressure. The title product is obtained in hydrochloride dihydrate form by crystallization from an ethanol solution.

M.p. 290–293° C.

Preparation 4

4-tert-Butoxycarbonylamino-1-(4-ethoxycarbonylphenyl)piperidine 21.6 g (0.10 mol) of the product from preparation 1 are heated at 80° C. for 55 hours with 9.06 g (0.01 mol) of (4-ethoxycarbonyl-1-fluoro)benzene and 14.9 g of $K_2CO_3$ in 200 ml of dimethylformamide. The $K_2CO_3$ is filtered off, the solution is poured into water and extracted with ethyl acetate, and the solvent is evaporated. The crude reaction product is purified by flash chromatography, elution being carried out with a cyclohexane/ethyl acetate=8:2 mixture. The title product is obtained and is crystallized from ethyl acetate.

M.p. 138–140° C.

Preparation 5

4-Amino-1-(4-ethoxycarbonylphenyl)piperidine hydrochloride 7.94 g (0.023 mol) of the product from preparation 4 are dissolved in 60 ml of ethyl acetate, and 80 ml of a 3N solution of hydrochloric acid in ethyl acetate are added. The mixture is heated at reflux for 5 hours, the solvent is evaporated, acetone is added and filtration is carried out. The title product is obtained and is crystallized from ethanol.

M.p. 240–242° C. (hydrochloride)

Preparation 6

4-tert-Butoxycarbonylamino-1-(4-methoxycarbonylphenyl)piperidine 3 mg (0.01 mmol) of $Pd(OAc)_2$, 10 mg (0.015 mmol) of 2,2'-bis(diphenylphosphino)-1,1'-binaphthyl (BINAP), 215 mg (1.2 mmol) of 4-bromo-1-methoxycarbonylbenzene and 240 mg of the product from preparation 1 (1.2 mmol) are added to a suspension of 456 mg of $Cs_2CO_3$ in 2 ml of anhydrous toluene. The mixture is heated at 110° C. and, after 2 days, 2 ml of dioxane, 3 mg of $Pd(OAc)_2$ and 10 mg of BINAP are added. The mixture is heated for a further two days at 110° and then the reaction is halted. The mixture is poured into water and extracted with ethyl acetate. The product is purified by flash chromatography, elution being carried out with an ethyl acetate/cyclohexane mixture.

M.p. 162–165° C.

Preparation 7

4-(Phenylmethoxy)-3-(N-tert-butoxycarbonyl-N-methansulfonylamino)-1-(2,3-epoxypropoxy)benzene and its (2S) isomer The title product was obtained according to the procedure disclosed in WO 96/04233 (procedure 96).

Preparation 8

4-Benzyloxy-3-methylsulfinyl-1-[(2,3-epoxypropoxy)]-benzene

The title product was obtained following the procedure disclosed in U.S. Pat. No. 4,396,629.

Preparation 9

4-Benzyloxy-1-[(2,3-epoxypropoxy)]benzene

The title product was obtained following the procedure disclosed in WO 96/04233 (procedure 7).

Preparation 10

4-tert-Butoxycarbonylamino-1-(4-hydroxycarbonylphenyl)piperidine 2.19 g (0.0063 mol) of the product from preparation 4 are dissolved in 30 ml of ethanol and 30 ml of THF, and 20 ml of water and 12.6 ml (0.0126 mol) of a 1N NaOH solution are added thereto. The mixture is stirred at ambient temperature for 24 hours and then at 40° C. for 8 hours. Acetic acid is added until a pH of 5 is achieved and the solvent is evaporated under reduced pressure. The residue is taken up in water and the solid is filtered off and recrystallized from 200 ml of ethanol. The title product is obtained in the form of a white solid.

M.p. >300° C.

Preparation 11

4-Amino-1-[4-(N-normal-butylaminocarbonyl)phenyl]-piperidine hydrochloride hydrate 11a. 4-tert-Butoxycarbonylamino-1-[4-(N-normal-butylaminocarbonyl)phenyl]piperidine 2.5 g (0.0078 mol) of the product from preparation 10 are dissolved in 80 ml of methylene chloride, and 3.45 g (0.0078 mol) of BOP, 8 ml (0.0078 mol) of normal-butylamine and 1.7 ml (0.012 mol) of triethylamine are added thereto. The mixture is stirred at 40° C. for 8 hours, the solvent is evaporated under reduced pressure, and the residue is taken up in ethyl acetate and washed with a saturated sodium bicarbonate solution. The solid formed is filtered off and crystallized from isopropanol. The title compound is obtained in the form of a white solid.

M.p. 208–210° C.

11b. 4-Amino-1-[4-(N-normal-butylaminocarbonyl)phenyl]-piperidine hydrochloride hydrate By carrying out the operation as described in preparation 5 but using the product from the preceding stage instead of the product from preparation 4, the title compound is obtained.

M.p. 231–235° C. (hydrochloride hydrate)

Preparation 12

4-Amino-1-[4-(N,N-diethylaminocarbonyl)phenyl]-piperidine dihydrochloride 12a. 4-tert-Butoxycarbonylamino-1-[4-(N,N-diethylaminocarbonyl)phenyl]piperidine By carrying out the operation as described in preparation 11a but using diethylamine instead of normal-butylamine, the title compound is obtained.

M.p. 113–115° C.

12b. 4-Amino-1-[4-(N,N-diethylaminocarbonyl)phenyl]-piperidine dihydrochloride

By carrying out the operation as described in preparation 11b but using the product from the preceding stage instead of the product from preparation 11a, the title compound is obtained.

M.p. 232–234° C. (dihydrochloride)

Preparation 13

4-Benzyloxy-3-(N-tert-butoxycarbonyl-N-(butansulfonyl)amino)-1-[((2S)-2,3-epoxypropoxy)]benzene 13a. 4-Benzyloxy-3-(butansulfonylamino)benzene acetate 5.0 g (0.00194 mol) of 3-amino-4-benzyloxybenzene acetate are mixed under a nitrogen atmosphere in 15 ml of methylene chloride, and 3.3 ml of triethylamine (0.0236 mol) and 3.3 ml (0.0245 mol) of 1-butansulfonyl chloride are added thereto. The mixture is stirred at ambient temperature overnight and afterwards at 30° C. for 4 hours. Washing with water is carried out, the two phases are separated, the organic phase is dried over sodium sulfate and filtered, and the solvent is evaporated under reduced pressure. Purification is carried out by chromatography on a column of silica gel, elution being carried out with a cyclohexane/ethyl acetate=9:1 mixture. The title compound is obtained.

M.p. 104–106° C.

13b. 4-Benzyloxy-3-(N-tert-butoxycarbonyl-N-(butansulfonyl)amino)benzene acetate 3.4 g (0.009 mol) of the product from the preceding stage are mixed in 70 ml of methylene chloride, and 2.4 g (0.0108 mol) of di-tert-butyl dicarbonate and 0.22 g (0.0018 mol) of 4-dimethylaminopyridine are added thereto. The mixture is stirred at ambient temperature for 3 hours, the solvent is evaporated and the residue is purified by chromatography on a column of silica gel, elution being carried out with a cyclohexane/ethyl acetate=8:2 mixture. The title compound is obtained.

M.p. 74–76° C.

13c. 4-Benzyloxy-3-(N-tert-butoxycarbonyl-N-(butansulfonyl)amino)phenol 4 g (0.0083 mol) of the product from the preceding stage are mixed in 80 ml of methanol, and 9.9 g (0.0099 mol) of 1N NaOH are added thereto. The mixture is stirred at ambient temperature for 30 minutes, citric acid is added until a pH of 6 is achieved and the solvent is evaporated. The residue is taken up with ethyl acetate, washing with water is carried out, the two phases are separated, the organic phase is dried over sodium sulfate and filtered, and the solvent is evaporated under reduced pressure. The title compound is obtained.

M.p. 131–133° C.

13d. 4-Benzyloxy-3-(N-tert-butoxycarbonyl-N-(butansulfonyl)amino)-1-[((2S)-2,3-epoxypropoxy)]benzene 3.0 g (0.0062 mol) of the product from the preceding stage are mixed in 60 ml of acetone, and 2.8 g of ground anhydrous potassium carbonate and 2.0 g (0.0077 mol) of (2S)-(+)-glycidyl nosylate are added thereto. The mixture is heated at reflux for 20 hours and filtered, the solvent is evaporated and the residue is purified by chromatography on a column of silica gel, elution being carried out with a cyclohexane/ethyl acetate=75/25 mixture. The title compound is obtained.

M.p. 87–89° C. $[\alpha]_D$=+4.9° C. (c, 1% in methanol)

Preparation 14

4-Benzylcarbonyloxy-3-(N-tert-butoxycarbonyl-N-propansulfonylamino)-1-[((2S)-2,3-epoxypropoxy)]benzene By carrying out the operation as described in preparation 13 but using 1-propansulfonyl chloride instead of 1-butansulfonyl chloride, the title compound is obtained.

$[\alpha]_D$=+4.5° C. (c, 1% in ethanol)

Preparation 15

4-Benzyloxy-3-(N-methylaminosulfonyl)-1-[((2S)-2,3-epoxypropoxy)]benzene]

15a. 2,5-Dihydroxy-N-methylbenzenesulfonamide 2.27 g (7.75 mmol) of 4-acetyloxy-2-(chlorosulfonyl)phenyl acetate, as obtained according to the process described in J. Am. Chem. Soc., 1951, 73, 2558–2565, are stirred at ambient temperature for 2 hours in 8 ml of tetrahydrofuran and 8 ml of a solution of methylamine (77.5 mmol) in methanol. The solvent is evaporated and the residue is taken up in 10 ml of acidified water. Extraction is carried out with ethyl acetate, the two phases are separated, the organic phase is dried over sodium sulfate and filtered, and the solvent is evaporated under reduced pressure. Purification is carried out by chromatography on a column of silica gel, elution being carried out with a hexane/ethyl acetate=1/2 mixture. The title compound is obtained.

15b. 2-Hydroxy-5-[[tert-butyl(dimethyl)silyl]oxy]-N-methylbenzenesulfonamide 1.07 g (7.10 mmol) of tert-butyldimethylsilyl chloride (TBDMSCl) and 1.76 ml of 1,8-diazabicyclo-[5.4.0]undec-7-ene (DBU) are mixed and this mixture is added to a solution of 1.4 g (6.9 mmol) of the product from the preceding stage in 20 ml of methylene chloride and 5 ml of tetrahydrofuran. The mixture is stirred at ambient temperature for 2 hours. Washing is carried out with water and with 20 ml of a 5% $H_3PO_4$ solution and, afterwards, with a sodium bicarbonate solution. The two phases are separated, the organic phase is dried over sodium sulfate and filtered, and the solvent is evaporated under reduced pressure. The title compound is obtained.

15c. 4-[[tert-Butyl(dimethyl)silyl]oxy]-2-(N-methylaminosulfonyl)phenyl benzoate 1.8 g (5.67 mmol) of the product from the preceding stage are mixed under a nitrogen atmosphere in 10 ml of methylene chloride, and 1.8 ml of pyridine and 1.3 ml of benzoyl chloride at 0° C. are added thereto. The mixture is stirred at ambient temperature for 3 hours and then a sodium bicarbonate solution is added thereto. Extraction is carried out with ethyl acetate, the two phases are separated, the organic phase is dried over sodium sulfate and filtered, and the solvent is evaporated under reduced pressure. The residue is purified by chromatography on a column of silica gel, elution being carried out with a hexane/ethyl acetate=2/1 mixture. The title compound is obtained.

15d. 4-Hydroxy-2-(N-methylaminosulfonyl)phenyl benzoate 1.7 g (4.03 mmol) of the product from the preceding stage are mixed under a nitrogen atmosphere in 80 ml of a 1% solution of hydrochloric acid in 95% ethanol. The mixture is stirred at ambient temperature for 3 hours. 100 ml of water are added thereto, extraction is carried out with ethyl acetate, the two phases are separated, the organic phase is dried over sodium sulfate and filtered, and the solvent is evaporated under reduced pressure. The title compound is obtained.

M.p. 168–170° C.

15e. 4-Benzyloxy-3-(N-methylaminosulfonyl)-1-[((2S)-2,3-epoxypropoxy)]benzene

By carrying out the operation as described in preparation 13d but using the product from the preceding stage instead of the product from stage 13c, the title compound is obtained.

$[\alpha]_D$=+19.9° (c=1% in chloroform)

Preparation 16

4-tert-Butoxycarbonylamino-1-(4-cyanophenyl)piperidine

By carrying out the operation as described in preparation 6 but using 4-bromocyanobenzene instead of 4-bromo-1-methoxycarbonylbenzene, the title compound is obtained.

M.p. 188–189° C.

Preparation 17
4-Amino-1-(4-cyanophenyl)piperidine

By carrying out the operation as described in preparation 5 but using the product from preparation 16 instead of the product from preparation 4. The base is released with ammonia and extraction with ethyl acetate, the title compound is obtained.

M.p. 78–80° C.

Preparation 18
4-tert-Butoxycarbonylaminomethyl-1-(4-ethoxycarbonylphenyl)piperidine By carrying out the operation as described in preparation 4 but using 4-(tert-butoxycarbonylaminomethyl)piperidine (disclosed in WO 99/65895) instead of the 4-(tert-butoxycarbonylamino)piperidine of preparation 1, the title compound is obtained.

Preparation 19
4-Aminomethyl-1-(4-ethoxycarbonylphenyl)piperidine hydrochloride

By carrying out the operation as described in preparation 5 but using the product from preparation 18 instead of the product from preparation 4, the title compound is obtained.

Preparation 20
4-Benzyloxy-3-(N-benzyloxycarbonyl-N-methansulfonylamino)-1-[((2S)-2,3-epoxypropoxy)]benzene 20a. 4-Benzyloxy-3-(N-benzyloxycarbonyl-N-methansulfonylamino)benzene acetate 1 g (0.003 mol) of 4-benzyloxy-3-(methansulfonylamino)benzene acetate (WO 96/04233) in 20 ml of methylene chloride, 0.50 ml (0.0033 mol) of 95% benzyl chloroformate, 0.006 g of dimethylaminopyridine and 0.46 ml (0.0033 mol) of triethylamine is stirred at 50° C. for 10 hours. The solvent is evaporated, the residue is taken up in methylene chloride, washing with water is carried out, the two phases are separated, the organic phase is dried over sodium sulfate and filtered, and the solvent is evaporated under reduced pressure. Purification is carried out by chromatography on a column of silica gel, elution being carried out with ethyl acetate. The title compound is obtained.

M.p. 140–142° C.

20b. 4-Benzyloxy-3-(N-benzyloxycarbonyl-N-methansulfonylamino)phenol

By carrying out the operation as described in preparation 13c but using the product from the preceding stage instead of the product from preparation 13b, the title compound is obtained.

M.p. 138–140° C.

20c. 4-Benzyloxy-3-(N-benzyloxycarbonyl-N-methansulfonylamino)-1-[((2S)-2,3-epoxypropoxy)]benzene By carrying out the operation as described in preparation 13d but using the product from the preceding stage instead of the product from stage 13c, the title compound is obtained.

M.p. 78–80° C.; $[\alpha]_D$=+4.4° (c=0.5% in methanol)

Preparation 21
4-Amino-1-(4-tert-butoxycarbonylphenyl)piperidine 1.5 g (7.5 mmol) of 4-(2,5-dimethylpyrrol-1-yl)piperidine, 60 ml of dimethylformamide and 1.6 g (7.5 mmol) of the tert-butyl ester of 4-fluorobenzoic acid and 2.6 ml of diisopropylethylamine are mixed under nitrogen. The mixture is heated with stirring for 6 hours at 90° C. and afterwards is stirred at ambient temperature for 15 hours. 1.04 g (7.5 mmol) of potassium carbonate are added thereto and the mixture is heated at 90° C. for 5 days. The mixture is poured into water, extraction is carried out with ethyl acetate and washing is carried out with water. The two phases are separated, the organic phase is dried over sodium sulfate and filtered, and the solvent is evaporated under reduced pressure. Purification is carried out by chromatography on a column of silica gel, elution being carried out with a hexane/ethyl acetate=3/1 mixture. 4-(2,5-Dimethylpyrrol-1-yl)-1-(tert-butoxycarbonylphenyl)piperidine is isolated. 250 mg of NH$_2$OH.HCl and 0.7 ml of ethanol are mixed under nitrogen and stirred for 30 minutes. 67 mg (1.2 mmol) of KOH in 0.3 ml of a 1/1 ethanol/water solution and 300 mg (0.084 mmol) of the above intermediate product in 0.5 ml of ethanol are added thereto. The mixture is heated at 80° C. for 12 hours. Extraction is carried out with ethyl acetate, KOH is added to the aqueous phase until a pH of 9 is achieved, and extraction is carried out with ethyl acetate. The two phases are separated, the organic phase is dried over sodium sulfate and filtered, and the solvent is evaporated under reduced pressure. The title compound is obtained.

M.p. 89–91° C.

Preparation 22
4-tert-Butoxycarbonylamino-1-(4-aminocarbonylphenyl)piperidine

By carrying out the operation as described in preparation 4 but using 4-fluorobenzamide instead of 4-ethoxycarbonyl-1-fluorobenzene, the title compound is obtained.

M.p. >270° C.

Preparation 23
4-Amino-1-(4-aminocarbonylphenyl)piperidine hydrochloride

By carrying out the operation as described in preparation 5 but using the product from preparation 22 instead of the product from preparation 4, the title compound is obtained.

EXAMPLE 1

3-[1-(4-Ethoxycarbonylphenylmethyl)piperidin-4-ylamino]-1-(4-hydroxyphenoxy)-2-propanol 1a. 3-[1-(4-Ethoxycarbonylphenylmethyl)piperidin-4-ylamino]-1-(4-methoxyethoxymethoxyphenoxy)-2-propanol 0.86 g (0.0033 mol) of 4-(methoxyethoxymethoxy)-1-(2,3-epoxypropoxy)benzene and 0.83 g (0.0033 mol) of the product obtained in preparation 3 in the free base form are heated at reflux for 17 hours in 40 ml of ethanol. The solvent is evaporated under reduced pressure and the product is dried. The crude reaction product is purified by flash chromatography, elution being carried out with methanol. The product is crystallized from isopropyl ether.

M.p. 73–75° C.

1b. 3-[1-(4-Ethoxycarbonylphenylmethyl)piperidin-4-ylamino]-1-(4-hydroxyphenoxy)-2-propanol dioxalate A mixture comprising 0.7 g (0.0014 mol) of the product obtained in the preceding stage and 1.1 ml (0.014 mol) of CF$_3$COOH in 40 ml of methylene chloride is heated at 40° C. for 8 hours. The solvent is evaporated and ammonia is added. Extraction is carried out with ethyl acetate, the extract is dried and the solvent is evaporated. The crude reaction product is purified by flash chromatography, elution being carried out with methylene chloride/methanol=9:1. The title compound is obtained in the base form. Its dioxalate is prepared using oxalic acid in acetone.

M.p. 180–184° C. (dioxalate)

EXAMPLE 2

3-[1-(4-Ethoxycarbonylphenyl)piperidin-4-ylamino]1-1(4-hydroxyphenoxy)-2-propanol 2a. 3-[1-(4-Ethoxycarbonylphenyl)piperidinylamino]-1-(4-benzyloxyphenoxy)-2-propanol 1.03 g (0.004 mol) of the product from preparation 9 and 1 g (0.004 mol) of the product from preparation 5 in the base form are heated at reflux for 20 hours in 50 ml of ethanol. The solvent is evaporated and the crude reaction product is purified by flash chromatography, elution being carried out with the $CH_2Cl_2$/methanol=9:1 mixture. The title product is obtained.

M.p. 112–114° C.

2b. 3-[1-(4-Ethoxycarbonylphenylmethyl)piperidin-4-ylamino]-1-(4-hydroxyphenoxy)-2-propanol 1.15 g (0.0023 mol) of the product from the preceding stage are hydrogenated at 40° C. in 20 ml of ethanol+20 ml of THF in the presence of 0.1 g of 10% palladium-on-carbon at ambient pressure for eight hours. 150 ml of hydrogen are absorbed.

The mixture is filtered and the solvent is evaporated. The residue is crystallized from ethyl acetate. The title product is obtained.

M.p. 158–161° C.

EXAMPLE 3

3-[1-(4-Ethoxycarbonylphenyl)piperidin-4-ylamino]-1-[(4-hydroxy)-3-(methansulfonylamino)phenoxy]-2-propanol and its (2S) isomer 3a. 3-[1-(4-Ethoxycarbonylphenyl)piperidin-4-ylamino]-1-[(4-benzyloxy)-3-(methansulfonylamino)phenoxy]-2-propanol 1 g (0.004 mol) of the product from preparation 5 in the base form is mixed with 1.35 g (0.003 mol) of the product from preparation 7 and 0.2 g of lithium perchlorate in 50 ml of $CH_3CN$. The mixture is left stirring for 24 hours at ambient temperature and is then heated at 40° for eight hours.

The solvent is evaporated and the product thus obtained is treated at 40° C. for eight hours with a solution of hydrochloric acid in ethyl acetate. The solvent is evaporated, the residue is treated with an $NaHCO_3$ solution and extraction is carried out with ethyl acetate. The solvent is again evaporated and the crude reaction product is purified by flash chromatography, elution being carried out with a $CH_2Cl_2$/methanol=9:1 mixture. The title product is obtained.

M.p. 130–132° C.

3b. 3-[1-(4-Ethoxycarbonylphenyl)piperidin-4-ylamino]-1-[(4-hydroxy)-3-(methansulfonylamino)phenoxy]-2-propanol 0.8 g (0.0013 mol) of the product from the preceding stage are subjected to hydrogenation in the presence of 0.1 g of palladium-on-carbon (10%) in 15 ml of ethanol+15 ml of THF. After reacting for eight hours at 40° and at ambient pressure, the mixture is filtered and the solvent is evaporated. The crude reaction product is purified by flash chromatography, elution being carried out with a $CH_2Cl_2$/methanol=9:1 mixture. The title product is obtained and is crystallized from isopropanol.

M.p. 140–143° C.

Isomer (2S)

By carrying out the operation according to the above stages 3a and 3b but using the product from preparation 7 in the optically active (2S) form, the (2S) enantiomer of the title compound is obtained.

M.p. 96–99° C. (hydrated form).

EXAMPLE 4

3-[1-(4-Ethoxycarbonylphenyl)piperidin-4-ylamino]-1-[(4-hydroxy)-3-(methysulfinyl)phenoxy]-2-propanol and its (2S) isomer 4a. 3-[1-(4-Ethoxycarbonylphenyl)piperidin-4-ylamino]-1-[(4-benzyloxy)-3-(methysulfinyl)phenoxy]-2-propanol 0.8 g (0.0032 mol) of the product from preparation 5 in the base form is heated at reflux overnight with 1 g (0.0031 mol) of the product from preparation 8 in 50 ml of ethanol. The solvent is evaporated and the crude reaction product is purified by flash chromatography, elution being carried out with a $CH_2Cl_2$/methanol=95:5 mixture. The title product is obtained.

M.p. 135–137° C.

4b. 3-[1-(4-Ethoxycarbonylphenyl)piperidin-4-ylamino]-1-[(4-hydroxy)-3-(methysulfinyl)phenoxy]-2-propanol trifluoroacetate 0.98 g (0.0017 mol) of the product from the preceding stage is heated at 55° C. for seven hours in 20 ml of $CF_3COOH$. The solvent is evaporated, a bicarbonate solution is added and extraction is carried out with ethyl acetate. The solvent is evaporated and the crude reaction product is purified by flash chromatography, elution being carried out with a $CH_2Cl_2$/methanol=9:1 mixture. The title product is obtained.

M.p. 78–80° C. (trifluoroacetate).

EXAMPLE 5

3-[1-(4-N-Butylaminocarbonylphenyl)piperidinylamino]-1-[(4-hydroxy)-3-(methansulfonylamino)phenoxy]-(2S)-2-propanol 5a. 3-[1-(4-N-Butylaminocarbonylphenyl)piperidinylamino]-1-[(4-benzyloxy)-3-(methansulfonylamino)phenoxy]-(2S)-2-propanol 0.72 g (0.0026 mol) of the product from preparation 11b in the base form is heated at reflux overnight with 1.08 g (0.0024 mol) of the product from preparation 7 in 25 ml of ethanol. The solvent is evaporated and the crude reaction product is purified by flash chromatography, elution being carried out with methanol. The product thus obtained is treated at 70° for 4 hours with a solution of hydrochloric acid in ethyl acetate. The solvent is evaporated, the residue is treated with an $NaHCO_3$ solution and extraction is carried out with ethyl acetate. The solvent is again evaporated. The title product is obtained.

M.p. 123–133° C.

5b. 3-[1-(4-N-Butylaminocarbonylphenyl)piperidin-4-ylamino]-1-[(4-hydroxy)-3-(methansulfonylamino)phenoxy]-(2S)-2-propanol By carrying out the operation as described in example 3b but using the product from the preceding stage instead of the product from stage 3a, the title compound is obtained.

M.p. 146–148° C.

EXAMPLE 6

3-[1-(4-N,N-Diethylminocarbonylphenyl)piperidiny-4-ylamino]-1-[(4-hydroxy)-3-(methansulfonylamino)phenoxy]]-(2S)-2-propanol By carrying out the operation as described in example 5 but using the product from preparation 12b in the base form instead of the product from preparation 11b, the title compound is obtained.

M.p. 67–70° C.

EXAMPLE 7

3-[1-(4-Ethoxycarbonylphenyl)piperidin-4-ylamino]-1-[(4-hydroxy)-3-(N-butansulfonylamino)phenoxy]-(2S)-2-propanol and its hydrochloride By carrying out the operation as described in example 5 but using the product from preparation 13d instead of the product from preparation 7 and the product from preparation 5 in the base form instead of the product from preparation 11b, the title compound is obtained. The hydrochloride is prepared using ethyl acetate and hydrochloric acid.

M.p. 192–195° C. (hydrochloride).

EXAMPLE 8

3-[1-(4-Ethoxycarbonylphenyl)piperidin-4-ylamino]-1-[(4-hydroxy)-3-(N-propansulfonylamino)phenoxy]-(2S)-2-propanol By carrying out the operation as described in example 5 but using the product from preparation 14 instead of the product from preparation 7 and the product from preparation 5 in the base form instead of the product from preparation 11b, the title compound is obtained.

M.p. 63–65° C.

EXAMPLE 9

3-[1-(4-Ethoxycarbonylphenyl)piperidin-4-ylamino]-1-[(4-hydroxy)-3-(methylaminosulfonyl)phenoxy]-(2S)-2-propanol 0.56 g (0.0015 mol) of the product from preparation 15e is heated at reflux overnight with 0.38 g (0.0015 mol) of the product from preparation 5 in the base form in 10 ml of DMF. The solvent is evaporated and the crude reaction product is purified by flash chromatography, elution being carried out with methanol. The title product is obtained.

M.p. 87° C.

EXAMPLE 10

3-[1-(4-Cyanophenyl)piperidin-4-ylamino]-1-[(4-hydroxy)-3-(N-methansulfonylamino)phenoxy]-(2S)-2-propanol By carrying out the operation as described in example 5 but using the product from preparation 17 instead of the product from preparation 11b, the title compound is obtained.

M.p. 78–80° C.

EXAMPLE 11

3-[1-(4-tert-Butoxycarbonylphenyl)piperidin-4-ylamino]-1-[(4-hydroxy)-3-(N-methansulfonylamino)phenoxy]-(2S)-2-propanol By carrying out the operation as described in example 3 but using the product from preparation 21 instead of the product from preparation 5 and the product from preparation 20 instead of the product from preparation 7, the title compound is obtained.

EXAMPLE 12

3-[[1-(4-Ethoxycarbonylphenyl)-4-piperidinylmethyl]amino]-1-[(4-hydroxy)-3-(methansulfonylamino)phenoxy]-(2S)-2-propanol By carrying out the operation as described as for example 5 but using the product from preparation 19 instead of the product from preparation 11b, the title compound is obtained.

EXAMPLE 13

5-[((4-Isopropylphenyl)sulfonyl)amino]-2-(4-((3-(4-hydroxyphenoxy)-2-hydroxypropyl)amino)piperidino)pyridine 13a. 5-Amino-2-(4-tert-butoxycarbonylaminopiperidino)pyridine 2 g (0.0062 mol) of 5-nitro-2-(4-tert-butoxycarbonylpiperidino)pyridine are mixed in 40 ml of ethanol and 60 ml of tetrahydrofuran. 0.4 g of 10% Pd/C are added and hydrogenation is carried out at 40° C. at ambient pressure for 7 hours. The mixture is filtered, the solvent is evaporated and 2 g of the title compound are obtained in the solid form.

13b. 5-[((4-Isopropylphenyl)sulfonyl)amino]-2-(4-tert-butoxycarbonylaminopiperidino)pyridine 0.4 g (0.0013 mol) of the product from the preceding stage is dissolved in 10 ml of pyridine. 0.3 g (0.0013 mol) of 4-isopropylbenzenesulfonyl chloride is added thereto and the mixture is heated at 50° C. for 2 hours. The solvent is evaporated (with the precautions for hydrochloric acid) and the residue is taken up in ethyl acetate and water. The two phases are separated, the organic phase is washed with water and dried, and the solvent is evaporated under reduced pressure. Purification is carried out by flash chromatography on a column of silica gel, elution being carried out with a cyclohexane/ethyl acetate=6/4 mixture. The title product is obtained.

M.p. 208–209° C.

13c. 5-[((4-Isopropylphenyl)sulfonyl)amino]-2-(4-aminopiperidino)pyridine dihydrochloride 2.1 g (0.0042 mol) of the product from the preceding stage are heated to reflux for 4 hours in 20 ml of ethyl acetate and 20 ml of an approximately 3N solution of gaseous hydrochloric acid in ethyl acetate. The solvent is evaporated under reduced pressure, the residue is taken up in acetone and filtered, the precipitate is washed with acetone and 1.8 g of the title product are obtained, which product is crystallized from ethanol.

M.p. 270–273° C.

13d. 5-[((4-Isopropylphenyl)sulfonyl)amino]-2-(4-((3-(4-(benzyloxy)phenoxy)-2-hydroxypropyl)amino)piperidino)pyridine 0.239 g (0.932 mol) of 4-benzyloxy-1-(2,3-epoxypropoxy)benzene and 0.35 g (0.935 mmol) of the product from the preceding stage in the base form are heated at reflux for 20 hours in 10 ml of ethanol. The solvent is evaporated under reduced pressure and purification is carried out by flash chromatography on a column of silica gel, elution being carried out with a methylene chloride/methanol=95/5 mixture. 0.37 g of the title product is obtained in the form of a glassy product.

13e. 5-[((4-Isopropylphenyl)sulfonyl)amino]-2-(4-((3-(4-hydroxyphenoxy)-2-hydroxypropyl)amino)piperidino)pyridine 0.37 g (0.586 mmol) of the product from the preceding stage, 10 ml of ethanol, 10 ml of tetrahydrofuran and 0.037 g of 10% Pd/C are mixed. Hydrogenation is carried out at 40° C. and ambient pressure for 8 hours. The mixture is filtered, the solvent is evaporated under reduced pressure and the residue is purified by flash chromatography on a column of silica gel, elution being carried out with a 9/1 methylene chloride/methanol mixture. The title product is obtained.

M.p. 75–78° C.

EXAMPLE 14

14a. 5-[((4-Isopropylphenyl)sulfonyl)amino]-2-(4-((3-(4-benzyloxy)-3-(methylsulfinyl)phenoxy)-2-hydroxypropyl)amino)piperidino)pyridine 0.27 g (0.00084 mol) of 4-benzyloxy-3-methylsulfinyl-1-[(2,3-epoxypropoxy)]benzene (prepared according to U.S. Pat. No. 4,396,629/example 3) and 0.33 g (0.00088 mol) of the product from example 13c) in the base form are heated at reflux overnight in 10 ml of ethanol. The solvent is evaporated and the crude reaction product is purified by flash chromatography, elution being carried out with a $CH_2Cl_2$/methanol=9/1 mixture. The title product is obtained in the form of a glassy solid.

14b. 5-[((4-Isopropylphenyl)sulfonyl)amino]-2-(4-((3-(4-hydroxy-3-(methylsulfinyl)phenoxy)-2-hydroxypropyl)amino)piperidino)pyridine 0.4 g (0.0006 mol) of the product from the preceding stage is heated at 55° C. for 5 hours in 10 ml of $CF_3COOH$. The solvent is evaporated under reduced pressure, the crude product is dissolved in ethyl acetate, washing is carried out using a saturated aqueous bicarbonate solution and drying is carried out. The product thus obtained is purified by flash chromatography, elution being carried out with a $CH_2Cl_2$/methanol=9/1 mixture and then with a $CH_2Cl_2$/methanol=85/15 mixture. The title product is obtained.

M.p.: 128–130° C.

EXAMPLE 15

5-[((4-Isopropylphenyl)sulfonyl)amino]-2-(4-((3-(4-hydroxy-3-methansulfonylamino)phenoxy)-(2S)-2-hydroxypropyl)amino)piperidino)pyridine By carrying out the operation as described in example 5 but using the product from example 13c in the base form instead of the product from preparation 11b, the title compound is obtained.

EXAMPLE 16

5-[((4-Bromophenyl)sulfonyl)amino]-2-(4-((3-(4-hydroxy-3-(methylsulfinyl)phenoxy)-2-hydroxypropyl)amino)piperidino)pyridine 16a. 5-[((4-Bromophenyl)sulfonyl)amino]-2-[4-(tert-butoxycarbonylamino)piperidino]pyridine By carrying out the operation as in example 13b but using 4-bromobenzenesulfonyl chloride instead of 4-isopropylbenzenesulfonyl chloride, the title compound is obtained.

16b. 5-[((4-Bromophenyl)sulfonyl)amino]-2-(4-((3-(4-hydroxy-3-(methylsulfinyl)phenoxy)-2-hydroxypropyl)amino)piperidino)pyridine By carrying out the operation as in example 13c, the product from the preceding stage is deprotected. 1.2 g of this product, 1.12 ml of triethylamine and 0.738 g of 4-benzyloxy-3-methylsulfinyl-1-[(2,3-epoxypropoxy)]benzene (prepared according to U.S. Pat. No. 4,396,629/example 3) are heated at reflux for 12 hours in 100 ml of ethanol. The solvent is evaporated and purification is carried out by flash chromatography, elution being carried out with a $CH_2Cl_2$/methanol/$NH_3$=90/10/1 mixture. A mixture containing 680 mg of the product thus obtained and 30 ml of $CF_3COOH$ is heated at 55° C. for 5 hours. The solvent is evaporated and the residue is treated with a saturated sodium bicarbonate solution. Extraction is carried out with ethyl acetate, the extract is dried and the solvent is evaporated. The crude reaction product is purified by flash chromatography, elution being carried out with methylene chloride/methanol/$NH_3$=90/10/1. The title compound is obtained in the base form.

M.p. 147° C.

EXAMPLE 17

3-[1-(4-Ethoxycarbonylphenyl)piperidin-4-ylamino]-1-(4-hydroxy-3-(methylsulfonyl)phenoxy)-(2S)-2-propanol By carrying out the operation as described in example 14 but using 4-benzyloxy-3-methylsulfonyl-1-((2S)-2,3-epoxypropoxy)benzene (disclosed in WO 99/65895, ex. 67) instead of 4-benzyloxy-3-methylsulfinyl-1-[(2,3-epoxypropoxy)]benzene and the product from preparation 5 in the base form instead of the product from example 13c), the title compound is obtained.

M.p. 83–85° C.; $[\alpha]_D$=+1.00 (c=1% in methanol)

EXAMPLE 18

3-[1-[4-((4-Isopropylphenyl)sulfonylamino)phenyl]-piperidinylamino]-1-(4-hydroxy-3-(methansulfonylamino)phenoxy)-(2S)-2-propanol By carrying out the operation as described in example 5 but using 4-amino-1-[4-((4-isopropylphenyl)sulfonylamino)phenyl]piperidine instead of the product from preparation 11b, the title compound is obtained.

M.p. 90–93° C.

EXAMPLE 19

3-[1-[4-((4-Bromophenyl)sulfonylamino)phenyl]-piperidinylamino]-1-(4-hydroxy-3-(methansulfonylamino)phenoxy)-(2S)-2-propanol 0.95 g (0.0023 mol) of 4-amino-1-[4-((4-bromophenyl)sulfonylamino)phenyl]piperidine and 1.1 g (0.0024 mol) of the product from preparation 7, (2S) isomer, are heated under reflux for 12 hours in 100 ml of ethanol. The solvent is evaporated and purification is carried out by flash chromatography, elution being carried out with a $CH_2Cl_2$/methanol=80/20 mixture. A mixture containing 680 mg of the product thus obtained and 30 ml of $CF_3COOH$ is heated at 55° C. for 5 hours. The solvent is evaporated and the residue is treated with a saturated sodium bicarbonate solution. Extraction is carried out with ethyl acetate, the extract is dried and the solvent is evaporated. The crude reaction product is purified by flash chromatography, elution being carried out with methylene chloride/methanol 90/10. The title compound is obtained.

M.p. 105–108° C.

What is claimed is:
1. A compound of formula (I)

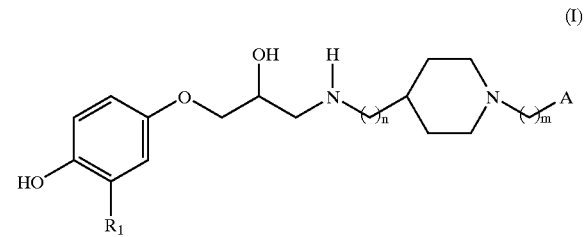

(I)

where
$R_1$ represents a hydrogen or halogen atom or an $—S(O)_z$—$(C_1-C_4)$alkyl, $—S(O)_z$—$(C_1-C_4)R_3$, $—SO_2$—NH—$(C_1-C_4)$alkyl, $—NHCO(C_1-C_4)$alkyl, $—CO(C_1-C_4)$alkyl or $—NHSO_2$—$(C_1-C_4)$alkyl group;

m and n independently represent 0, 1 or 2;

A represents a group of formula (a) or (b):

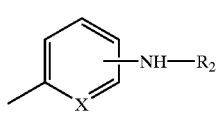

(a)

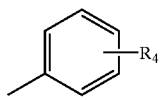

(b)

where
x is N or CH;
$R_2$ represents an —$SO_2$—$R_3$, —CO—$R_3$ or —CO—($C_1$–$C_4$)-alkyl group;
$R_3$ represents a phenyl group, optionally substituted by a ($C_1$–$C_4$)alkyl or ($C_1$–$C_4$)alkoxy group, one or two halogen atoms or a heterocycle;
$R_4$ represents a hydrogen or halogen atom or a ($C_1$–$C_6$) alkyl, ($C_1$–$C_4$)alkoxy, —COOH, —COO($C_1$–$C_4$)alkyl, —CN, —$CONR_5R_6$, —$NO_2$, or —$SO_2NR_5R_6$ group;
z is 1 or 2;
$R_5$ and $R_6$ independently represent a hydrogen atom or a ($C_1$–$C_4$)alkyl, phenyl or phenyl($C_1$–$C_4$)alkyl group;
or a salts or solvates thereof.

2. A compound according to claim 1, where A is a group (a), X is N and the $NHR_2$ group is in the 5 position of the pyridine.

3. A compound according to claim 1, where n and m are zero.

4. A compound according to claim 1, where the ($C_1$–$C_4$) alkyl group is a methyl or ethyl group.

5. A compound according to claim 1, where A is a group (b) and the $R_4$ group is in the 4 position of the benzene.

6. A compound according to claim 1, where A is a group (b) and $R_4$ is chosen from —COOH, —COOH$C_1$–$C_4$)alkyl, —CN, —$NO_2$, —$CONR_2R_3$, and —$SO_2NR_5R_6$.

7. A process for the preparation of the compounds of formula (I) wherein a compound of formula (II)

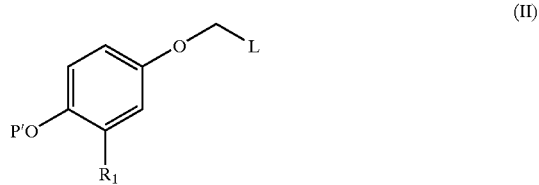

(II)

in which $R_1$ is as indicated in claim 1, P' is a protective group and L is a group of formula (c) or (d)

(c)

(d)

where Gp is a leaving group, is reacted with an amine of formula (III)

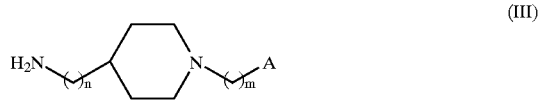

(III)

in which n and m are as defined in claim 1, the group P' being cleaved and the compound of formula (I) thus obtained optionally being converted into one of its salts.

8. A pharmaceutical composition comprising, as active principle an affective amount of the compound as claimed in claim 1.

9. A pharmaceutical composition comprising, as active principle, an effective amount of the compound as claimed in claim 2.

10. A pharmaceutical composition comprising, as active principle, an effective amount of the compound as claimed in claim 3.

11. A pharmaceutical composition comprising, as active principle, an effective amount of the compound as claimed in claim 4.

12. A pharmaceutical composition comprising, as active principle, an effective amount of the compound as claimed in claim 5.

13. A pharmaceutical composition comprising, as active principle, an effective amount of the compound as claimed in claim 6.

14. A method for the treatment of irritable bowel syndrome, for treating obesity, or for treating diabetes, which comprises administering to a patient in need of such treatment an effective amount of a compound according to claim 1.

15. A method for the treatment of irritable bowel syndrome, for treating obesity, or for treating diabetes, which comprises administering to a patient in need of such treatment an effective amount of a compound according to claim 2.

16. A method for the treatment of bowel syndrome, for treating obesity, or for treating diabetes, which comprises administering to a patient in need of such treatment an effective amount of a compound according to claim 3.

17. A method for the treatment of irritable bowel syndrome, for treating obesity, or for treating diabetes, which comprises administering to a patient in need of such treatment an effective amount of a compound according to claim 4.

18. A method for the treatment of irritable bowel syndrome, for treating obesity, or for treating diabetes, which comprises administering to a patient in need of such treatment an effective amount of a compound according to claim 5.

19. A method for the treatment of irritable bowel syndrome, for treating obesity, or for treating diabetes, which comprises administering to a patient in need of such treatment an effective amount of a compound according to claim 6.

20. A method according to claim 14 for the treatment of irritable bowel syndrome.

21. A method according to claim 15 for the treatment of irritable bowel syndrome.

22. A method according to claim 16 for the treatment of irritable bowel syndrome.

23. A method according to claim 17 for the treatment of irritable bowel syndrome.

24. A method according to claim 18 for the treatment of irritable bowel syndrome.

25. A method according to claim 19 for the treatment of irritable bowel syndrome.

* * * * *